United States Patent [19]

Kaye et al.

[11] 4,447,223
[45] May 8, 1984

[54] MEDICAMENT IMPLANT APPLICATOR

[75] Inventors: Gordon E. Kaye, Garrison, N.Y.; Eugene B. Schwartz, Miami Beach, Fla.; Irving V. Sollins, Jiutepec Morelos, Mexico

[73] Assignee: CCT Associates, Bethesda, Md.

[21] Appl. No.: 369,200

[22] Filed: Apr. 16, 1982

[51] Int. Cl.³ .............................................. A61M 5/18
[52] U.S. Cl. ......................................... 604/61; 604/62
[58] Field of Search ................ 604/62, 61, 60; 124/45

[56] References Cited

U.S. PATENT DOCUMENTS

| | | | |
|---|---|---|---|
| 3,520,299 | 7/1970 | Lott et al. | 604/62 X |
| 3,774,607 | 11/1973 | Schmitz | 604/61 |
| 4,004,565 | 1/1977 | Fischer et al. | 604/62 X |
| 4,077,406 | 3/1978 | Sandhage et al. | 604/612 X |
| 4,105,030 | 8/1978 | Kersco | 604/61 X |
| 4,154,239 | 5/1979 | Turkey | 604/62 X |

Primary Examiner—Stephen C. Pellegrino
Attorney, Agent, or Firm—Cantor and Lessler

[57] ABSTRACT

A pistol-shaped medicament implant applicator with a needle mounted on the forward end thereof, and a multichambered medicament cartridge adapted for insertion into the implant applicator wherein the applicator mechanism:

transports a plunger through one of the medicament containing chambers in the cartridge into the implant needle and forces medicament out the needle front;

moves the needle relative to an abutment on the front face of the applicator adapted to be held against the skin of the animal being implanted, the relative movement forcing withdrawal of the needle, resulting in deposition of the medicament in the needle track;

retracts the plunger so as to clear needle and cartridge; and, shifts the cartridge the spacing between adjacent chambers therein and indexes the next medicament containing cartridge chamber to the needle bore and the path of the plunger.

The cartridge is provided with cam tracks that in cooperation with the implanter mechanism shift and index successive cartridge chambers to the needle bore and the plunger path.

6 Claims, 22 Drawing Figures

MEDICAMENT IMPLANT APPLICATOR

The present invention relates to an implanter device adapted for insertion of a solid or semi-solid pellet form medicament into a domestic animal and a cassette containing a multiplicity of dosage unit pellets of the medicament.

INTRODUCTION

Good animal husbandry practices sometimes make desirable an insertion into the animal (e.g., intradermally, subcutaneously, intra-muscularly, etc.) of a solid or semisolid medicament. Such practice is common for growth stimulation of cattle, for example. The growth stimulating hormones in solid pellet form are implanted in the neck or ear of the animal, to remain there for an extended period, even throughout the life span of the animal. Implantation in the ear is a preferred site, since the ear is a throw-away organ. Any implant residue present in the ear when the animal is slaughtered never enters channels of commerce, to become ingested by people or domestic animals.

A typical medicament implant device comprises a hand-held instrument of a size consistent with the size of the animal (large for cattle, small for chickens), with an apertured needle tip constructed to make a sizable, non-coring puncture opening into the skin (e.g., ear) of the animal and form a cavity opening occupied by the needle portion of the instrument. The body of the instrument which may be a hand gun-like device is adapted to be a receiver-dispenser for the medicament implant. For cattle, an implant dosage unit form may constitute a multiplicity, e.g., eight, relatively small solid or semi-solid pellets.

A reciprocal plunger forces the pellets out of a cartridge encasement wherein they are prepackaged into the bore of the needle and from there into the animal body. A number of medicament implant devices have been suggested to the art, including pistol-like devices capable of using cartridges that contain a multiplicity of dosage unit implants.

The principal object of the present invention is to provide a novel implant applicator for implantation of pellets.

A further object of the invention is to provide a novel multi-dosage indexable cassette adapted for use in the implant applicator of this invention.

OPERATION OF THE APPLICATOR GUN AND CASSETTE

The novel pellet implant cassette or cartridge of this invention contains two rows of equally spaced chambers, e.g., 10 chambers per row, with each chamber sized to contain therein a dosage unit of medicament, e.g., eight pellets, which allows then, the animal handler to implant animals in quick succession, e.g., 10 animals one after another. Then the handler reverses the cassette in the implant applicator and implants another set of animals in quick succession from the other row in the same cartridge.

The implant applicator mechanism automatically expels the implant medicament pellet(s) from the chamber of the cartridge into a needle at the forward end of the applicator, and then expels the medicament pellets as the mechanism also forces withdrawal of the needle from the animal into which the needle had previously been inserted, thereby implanting the pellet(s) in the needle track. The plunger then retracts and thereafter, the applicator mechanism shifts the cassette transversely so that a next adjacent chamber of the cassette moves into registry with the needle and the plunger for a future expulsion of medicament therefrom.

THE IMPLANT APPLICATOR GUN AND MEDICAMENT CASSETTE

For further understanding of this invention, reference is now made to the attached drawings wherein:

FIG. 16-20 are each a partial side section with selected parts taken away.
FIGS. 16-20 as a whole illustrating successive positions of the mechanism of the implant applicator during an implantation sequence.

Figure 1:
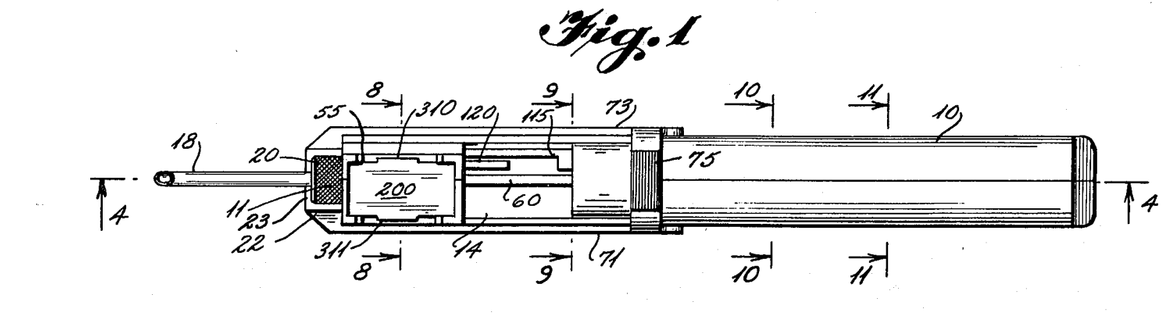
FIG. 1 is a plan view of the applicator.
Figure 2:
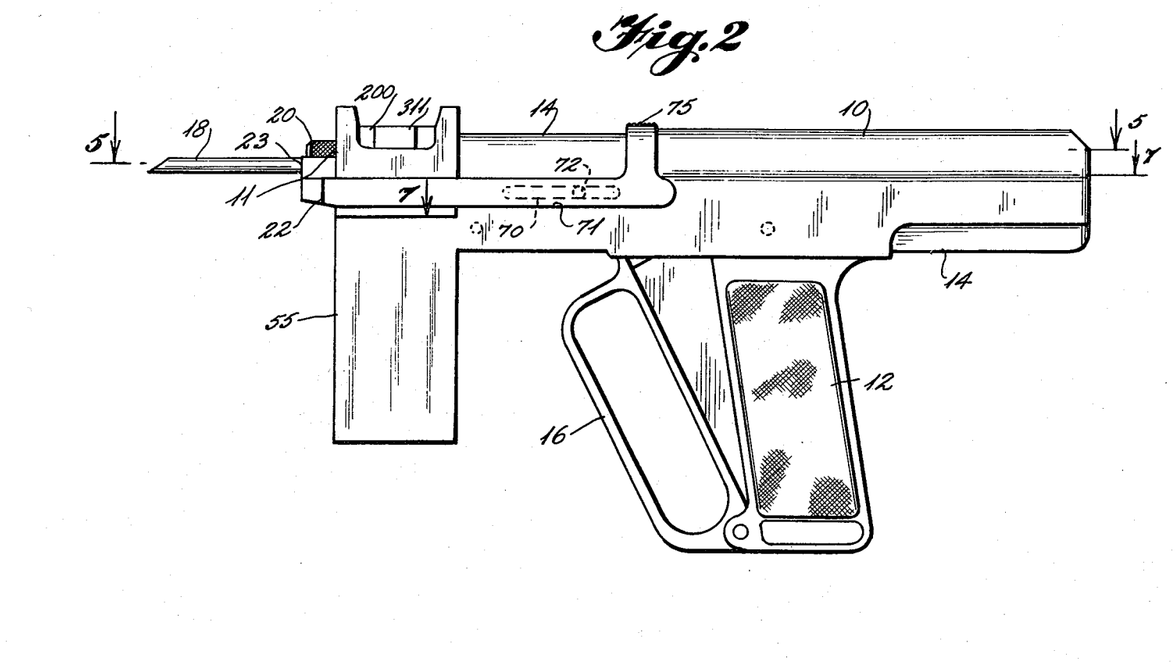
FIG. 2 is a side view of the applicator.
Figure 3:
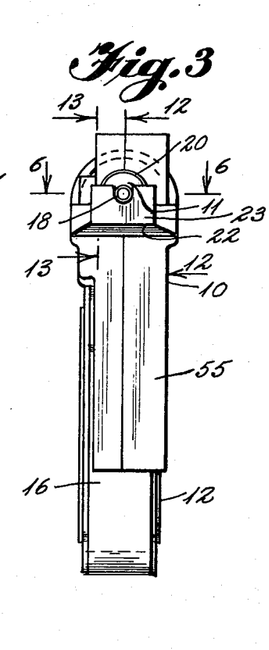
FIG. 3 is a front end view of the applicator.

Referring now to FIGS. 1, 2 and 3 of the drawing, it may be seen therein that the implant applicator 10 much resembles a pistol, having a pistol grip 12, a housing 14 and a trigger 16 on the pistol grip. On the forward end face 11 of applicator 10 is mounted a conventional implantation needle 18, i.e., a hollow, beveled edge needle, sized so that the medicament pellet(s) 3 to be implanted can pass from the needle rear through the bore of the needle 18 and out the front edge. Needle 18 is clamped to the forward end 11 of applicator 10 by a standard chuck mounting 20 (illustrated only in part).

Figure 16:
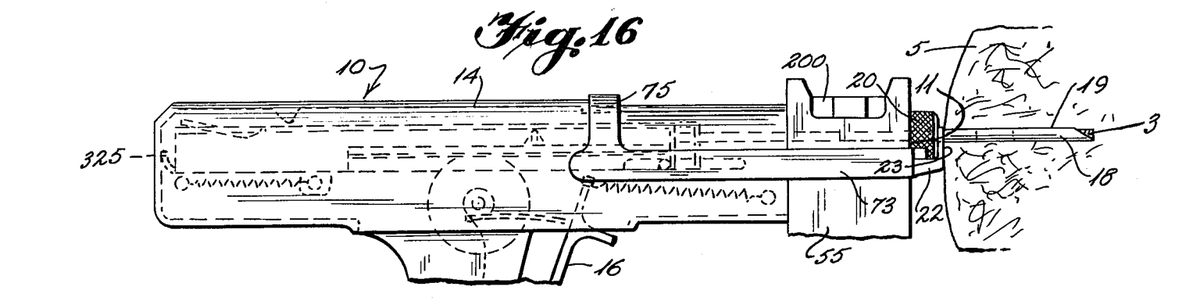
Figure 17:
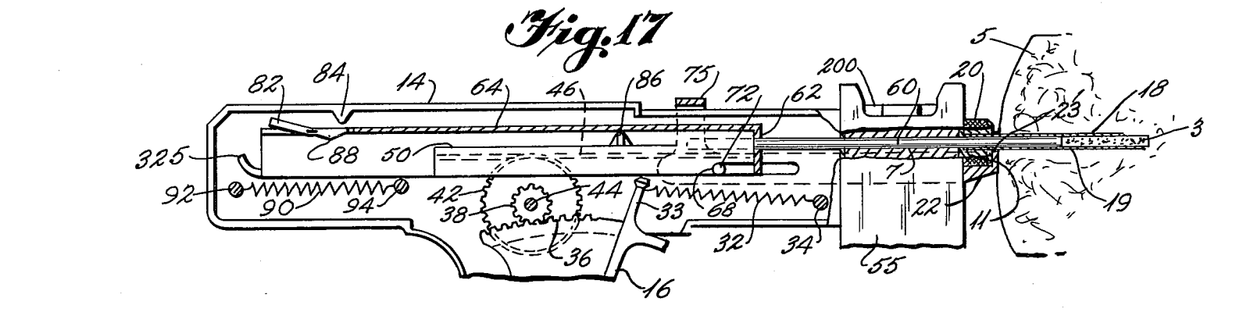
Figure 18:
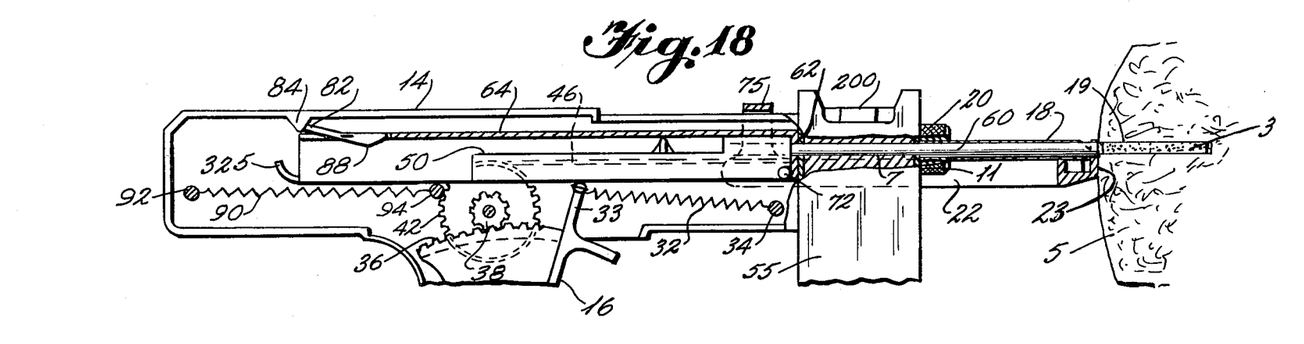
Figure 19:
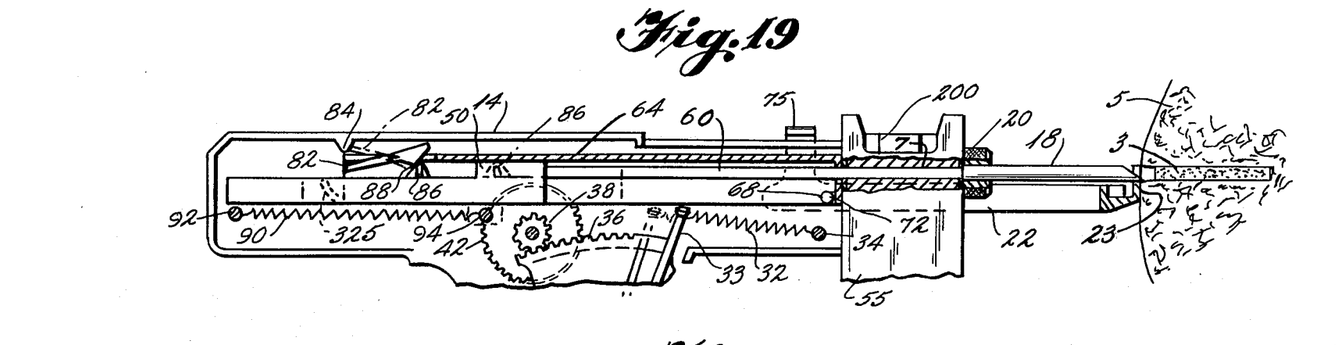

Thus, applicator 10 is adapted to be held comfortably by one hand so that the attached needle 18 may be inserted into an animal, e.g., subcutaneously, positioning the front face 23 of an extractor yoke 22 on applicator 10 flush against the animal's skin 5, as is illustrated in FIG. 16. When trigger 16 is pulled, the hereinafter described mechanism of the applicator impels the medicament implant pellet(s) 3 forward into needle 18, as is illustrated in FIG. 17, and then moves the yoke 22 forward, as is illustrated in FIGS. 18 and 19, thereby forcing withdrawal of the needle 18 from the animal skin 5. During withdrawal of needle 18, the pellet(s) 3 are expelled through the front end opening of the needle 18 into the needle track 19. Since the front face 23 on yoke 22 is held flush against the skin of the animal when trigger 16 is pulled, and subsequently, the movement actually generated by the mechanism is that implant applicator 10 as a whole including needle 18 moves rearward while the front face 23 of yoke 22 remains pressed in place and stationary against the skin of the animal. In any event, the needle 18 withdraws from the animal at the same time the pellet(s) 3 of the implant are expelled into the needle track to become implanted in the animal. As has already been indicated, FIGS. 16, 17, 18 and 19 generally illustrate the above described implantation of medicament pellets 3 beneath the skin 5 of an animal in the track 19 made by non-coring needle 18. The medicament pellet(s) 3 are transferred from chamber 7 of a medicament containing cassette 200 into needle track 19 by forward movement of plunger 60 through chamber 7 and needle 18.

Figure 20:
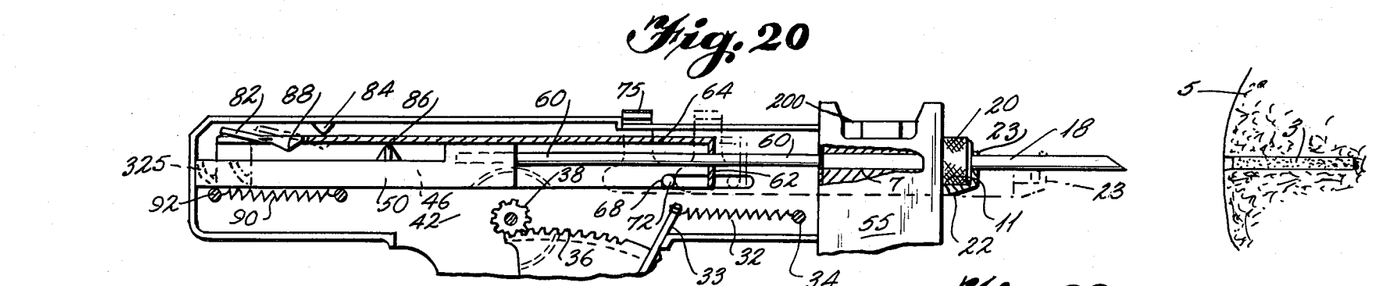

The retraction or return movement sequence of plunger 60, yoke 22, etc. as is illustrated by FIG. 20 takes place with retraction of trigger 16 by tension spring 32.

Associated with retraction of plunger 60 is a return movement of an indexing cam 120 which generates a transverse shift in the position of medicament cassette 200 within applicator 10, (an axially upward shift in the mode of cassette 200 and applicator 10 herein illustrated). The action of indexing cam 120 which will be hereinafter described can be seen in FIGS. 15, 21 and 22. The transverse shift places the next adjacent medicament chamber of cassette 200 into registry with needle 18 so that in the next implantation sequence plunger 60 will expel the pellet(s) from that chamber through needle 18.

Figures 12, 13:
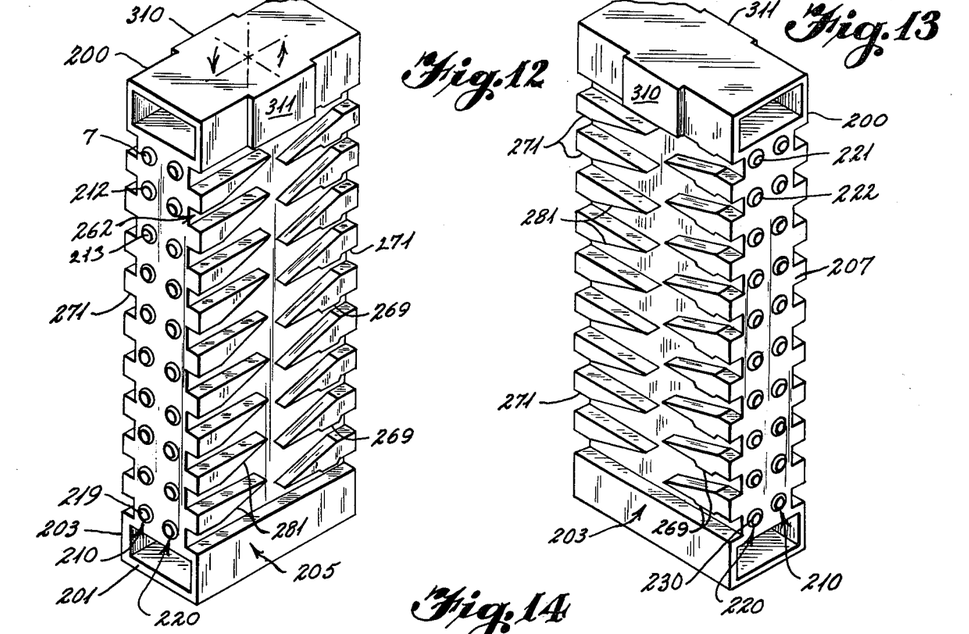
FIG. 12 is an isometric view of the cassette.
FIG. 13 is an isometric view of the cassette illustrating the face of the cassette not visible on FIG. 12.

The structure of cassette 200 is illustrated principally in FIGS. 12 and 13. FIG. 12 shows an isometric view of a preferred mode of cassette 200 from one side and FIG. 13 shows an isometric view from the obverse side, illustrating in total side faces 201, 203, 205, and 207 of cassette 200.

As is evident in FIGS. 12 and 13, cassette 200 has two rows, 210, 220, of passthrough (cylindrical) chambers; row 210 contains the chamber 7 and in succession chambers 212-219; and the other row contains chambers 221-230. Each chamber is, of course, size matched to the bore of needle 18, to the diameter of plunger 60 and to the quantity of medicament in a dosage unit of pellet(s) form.

Figure 4:
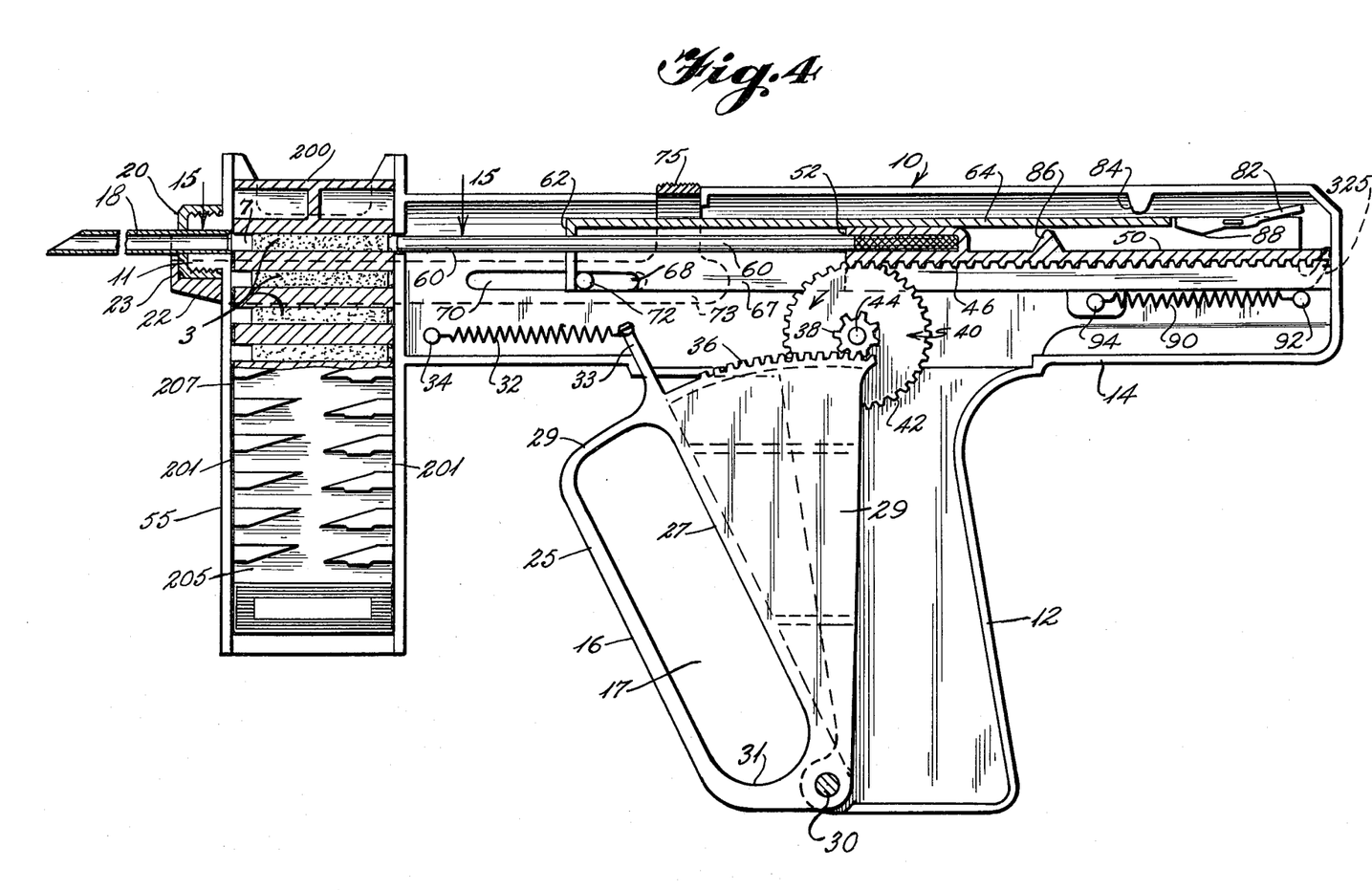
FIG. 4 is a side section taken through line 4—4 of FIG. 1.
Figure 5:
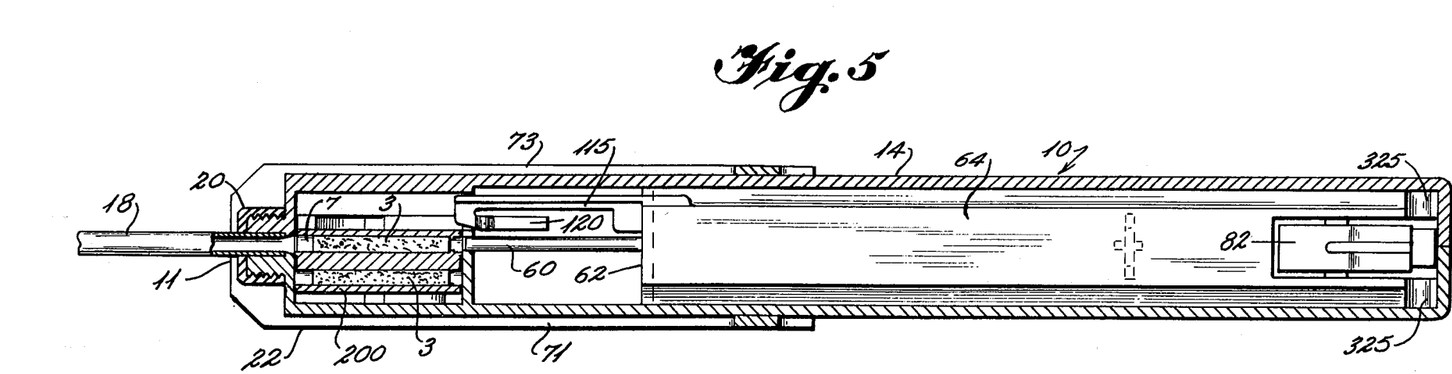
FIG. 5 is a top section taken through line 5—5 of FIG. 2.

Filling of such medicament cassettes with medicament pellets, and the expedients such as dimples 207 employed to retain the pellet(s) 3 inside the passthrough chambers form no part of this invention. Suffice it to note that standard packaging machinery and techniques are contemplated, as is employment of known-to-the-art medicament compositions for the implant pellets. Orienting keys such as, for example, projections 310 and 311 at the top of cassette 200 facilitate proper placement of cassette 200 into a housing 55 of applicator 10 (as shown by FIGS. 2 and 4).

On side faces 203 and 205 are cam patterns 240 and 250 that are the same, but reversed one from the other so that after the chamber 7 and 212-219 in row 210 have been emptied cassette 200 can be taken out of housing 55, then rotated 180° on its long axis and reinserted into applicator 10. Then the same cam pattern is presented to the mechanism in applicator 10 that shifts cassette upwardly, chamber by chamber, so as to empty row 220 chamber by chamber.

Many of the features described above for the preferred mode of cassette 200 herein illustrated may be varied without departing from the spirit of this invention. For example, the keys 310, 311 whose purpose is to orient cassette 200 for proper insertion into the cassette housing 55 of implant applicator 10 may be modified as desired. However, certain of the relationships in the structure of cassette 200 are essentially invarient, notably the spacing between adjacent cam patterns which spacing must always correspond to the distance between the adjacent medicament chambers in rows 210, 220 and the outside wall thickness (between chambers and the cam track) which thickness must correspond to the spacing distance between the cam 120 and the plunger 60 inside of applicator 10. However, so long as their functional interaction is as described herein, the actual details of the cam 120 and the cam patterns 203 and 205 may be modified. Also, the symmetry in cassette 200 around the long side axis described above may be replaced by a like symmetry of chamber rows and cam track around a short side axis so that reinsertion of cartridge 200 into implanter 10 to disharge medicament from the second row requires an appropriate top to bottom rotation for proper presentment of the cam track on the obverse side face to the mechanism of applicator 10.

Figure 15:
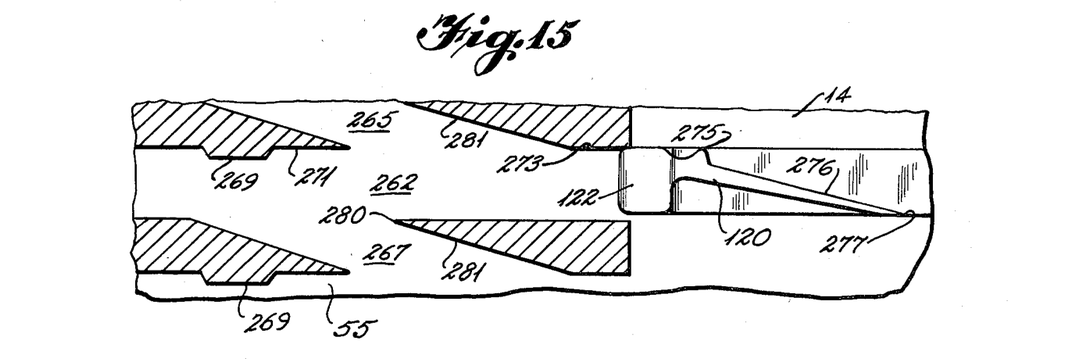
FIG. 15 is an enlarged partial section taken along line 15—15 of FIG. 14.
Figure 21:
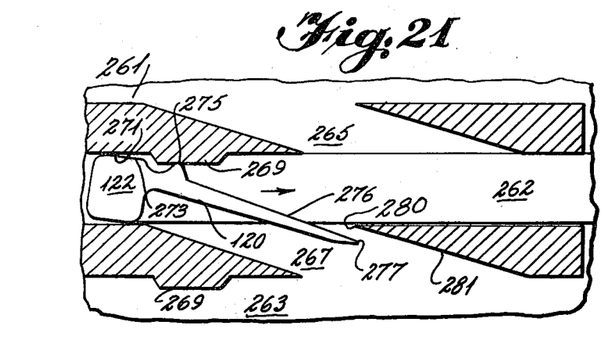
FIGS. 21 and 22 are the partial section of FIG. 15 illustrating cam movement during operation of the applicator.
Figure 22:
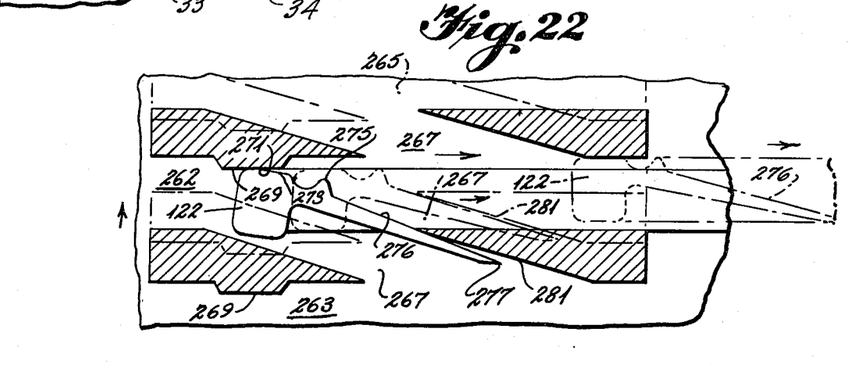

The operation of the cam patterns 203 and 205 on cassette 200 illustrated by the fragmentary views of FIGS. 15, 21 and 22. Thus, it may be seen thereon that each chamber in cassette 200 has associated therewith a passthrough cam track slot, slot 261 being associated with chamber 7, slot 262 with chamber 212, slot 263 with chamber 213, etc. Connecting each adjacent passthrough slot to the next lower slot is a diagonal slot such being more clearly illustrated in FIGS. 21 and 22 where can be seen that diagonal slot 265 connects passthrough slots 261 and 262, and diagonal cam track slot 267 connects passthrough cam track slot 262 to the next (lower) passthrough cam track slot 263. Near the front end of each passthrough cam track slot is a camming projection 269 that depends from the top wall of the slot.

Figure 14:
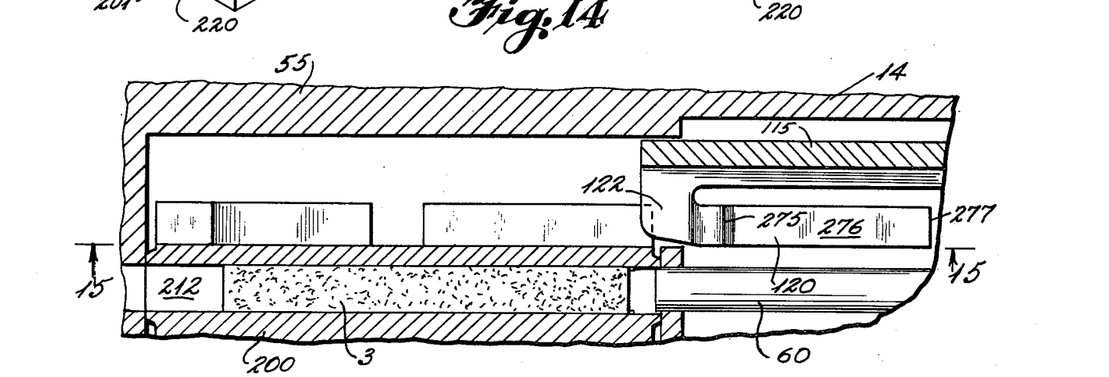
FIG. 14 is an enlarged partial section of the implanter front taken along the lines 14—14 on FIG. 2.

FIG. 14 illustrates the association of cam track slot with chamber, e.g., of cam track slot 262 to chamber 212. In the 'at rest' status of implanter 10, the cam 120 rests in the entrance to cam track slot 262, acting therein as a detente to align chamber 212 with plunger 60. When plunger 60 moves forward an index bar 64 on which cam 120 is mounted will also move forward from right to left, then after plunger 60 has withdrawn retraction of index bar 64 and cam 120 generate a transverse movement of cassette 200 exactly the one chamber spacing, as is illustrated by FIGS. 21 and 22.

Cam 120 is a flexible member which bends and twists elastically. A hook-like neck 122 attachment to index bar 64, and formation of cam 120 from a conventional flexible material allows elastic bending and torsional movement. Forces applied at the end 277 of the long lever arm 276 on cam 120 or along its length as for instance, at knob 275, will cause cam 120 to deflect (through torsion) at neck 122.

Rounded surfaces at the nose 122 of cam 120 together with the aforementioned flexibility to bend and/or deflect at neck 122 allows insertion of cassette 200 into applicator 10 with nose 122 positioned as a detent in the entrance portion of the uppermost slot 261. To repeat, seating of nose 122 of cam 120 in a slot e.g., 262 maintains the cassette chamber associated with that slot e.g., chamber 212 in registry with plunger 60, as is shown by FIG. 14. The cooperating surfaces for such registry are the top wall surface 271 of slot 262 and the top surface 273 of cam nose 122, all as shown in FIG. 15.

As may be seen then in FIGS. 21 and 22, when cam 120 moves forward toward the needle, the top surface 273 of nose 122 and the knob 275 of the cam ride forward along the slot wall top surface 271. Some clearance is provided at the slot floor, as is indicated in FIG. 15 so as to allow nose 122 and the cam as a whole to ride down around camming projection 269, bending at neck 122 to do so. However, once nose 122 has moved forward past camming projection 269 to the extreme forward position illustrated by FIG. 21, at which position the end 277 of lever arm 276 on cam 120 has cleared the entrance point 280 of diagonal slot 267, the knob 275 on cam lever arm 276 still rides on camming projection 269. When the cam 120 is at its most forward location, the forces on cam 120 are largely torsional causing the rotational deflection illustrated in FIG. 21 that swings the end 277 of cam arm 276 down past entrance point 280 of diagonal slot 267. Then a retraction movement, left to right by cam 120, will then cause cam 120 to ride on the upper surface 281 of the diagonal slot 267. Such reverse movement of cam 120 inside diagonal slot 267 takes place however, only after plunger 60 has withdrawn fully from cassette chamber 212. During reverse movement the cam 120 moves horizontally so that its travel along the upper surface 281 of diagonal slot 267 shifts cassette 200 transversely (the distance between adjacent passthrough cam slots). Finally, nose 122 of cam 120 comes to rest in its detent position in the entrance of passthrough cam track slot 263. The return movement of cam 120 and the transverse shift by cassette 200 are indicated in FIG. 22 by shadow lines.

The further description of the mechanism of applicator 10 which now follows is made with reference to FIGS. 4-11, principally with reference to FIG. 4, whereon the internals of applicator 10 is illustrated by a side section.

Referring once again to trigger 16, it may be seen that trigger 16 is formed as a hollow, generally rectangular finger space 17 bounded by a forward wall 25 and a rear wall 27 connected together by upper web 29 and lower web 31. At its lower rear corner trigger 16 is (pivotally) secured to pistol grip 12 by pivot pin 30. At the top of the rear wall 27 on trigger 16 is a tab 33 which extends up beyond web 29 into housing 14 through a slot 35 on the underside of the housing. At the terminus of tab 33 is mounted one end of (tension) spring 32. The other end of tension spring 32 is attached to a pin 34 on the inside wall of housing 14 (see also FIGS. 6 and 7). Trigger 16 is tensioned in its forward rest position by spring 32 and must be pulled against the spring tension to operate applicator 10. Spring 32 then acts as a return spring to return trigger 16 forward when finger pressure on trigger 16 is released. If the applicator mechanism should hang up, then forward wall 25 of trigger 16 may be pushed or pulled forward to return trigger 16 to its forward position.

Figure 10:
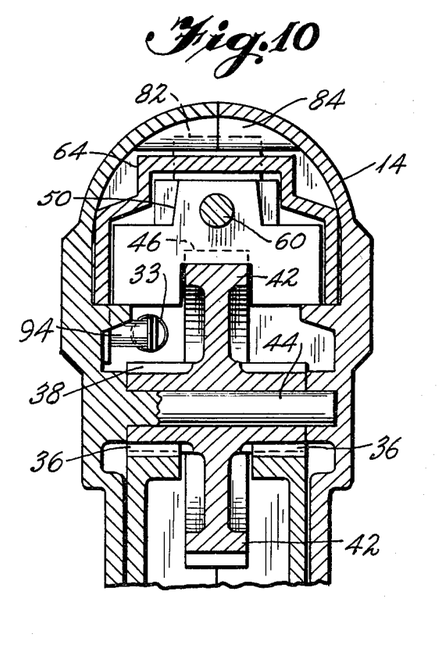
FIG. 10 is an end section taken through line 10—10 on FIG. 1.

Behind the rear wall 27 of trigger 16 and integral therewith is a web or frame 29 whose top surface is formed into a sector gear 36. When trigger 16 is pulled, sector gear 36 drives the pinion 38 of a combination gear 40, which in turn rotates bull gear 42. FIG. 10 illustrates how the combination gear 40 is rotatably mounted on pin 44, which in turn is seated in the side walls of housing 14. If desired, gear 40 may be fixed on pin 44 and pin 44 rotatably mounted in the side walls of housing 14. Sector gear 36 is split or slotted so as to allow bull gear 42 to be centered.

The teeth on bull gear 42 engage the rack 46 at the underside of a plunger rack bar 50, which means that bull gear 42 drives rack bar 50 forward when trigger 16 is pulled; the already described plunger 60 is integrally secured to the forward end of plunger rack bar 50 and then moves forward so as to expel the pellet(s) from the cassette chamber 7 through the bore of needle 18.

Mention already has been made that needle 18 has been fully inserted in the animal prior to pulling trigger 16, with the front face 23 of yoke 22 held against the skin, and that plunger 60 advances far enough to transfer the pellets of the medicament 3 into needle 18, (as is shown by FIGS. 16 and 17) desirably to near the tip end of needle 18 before any movement by yoke 22 forward relative to the applicator as a whole takes place, such yoke movement forcing withdrawal of needle 18 from the animal. The delayed movement of yoke 22 until after substantial forward movement of plunger 60 has happened and the distance forward traveled by yoke 22 (which distance corresponds generally to the length of needle 18), is provided by a lost motion connection between rack bar 50 and the yoke 22.

Ideally, the extractor yoke 22 will commence forward movement just as forward end of the medicament quantity has arrived at the tip of the needle, somewhat less desirably sooner. Simultaneous movement by extractor yoke 22 and plunger 60 continues until the needle 18 has been emptied of medicament 3, by virtue of plunger 60 coming to rest at the front end tip of needle 18. The simultaneous movement by yoke 22 and plunger 60 that causes the forward motion of the yoke 22 to withdraw needle 18 from the tissue while leaving behind in the needle track the medicament pellets, 3 being expelled through the needle by plunger 60 is considered to be an advantageous feature of this invention.

The delay between the initial forward movement of plunger 60 and commencement of movement by yoke 22 is created by (the lost motion connection) between a pair of slots 68 in index bar 64 which have delayed engagement with the pins 72 on the yoke 22 because cam bar 64 must first travel the length of the slots 72. The length of slots 72 is, of course, predetermined and correspond in length to how much of the plunger movement should be lost motion.

The forward movement of cam 120 incident to indexing of cassette 200 medicament chamber by medicament chamber also is tied to the forward movement of rack bar 50 and plunger 60 by a different and independent lost motion connection. Cam 120 travels a distance in the cam tracks of the cassette which need not be the same as the distance traveled by yoke 22. Also, it is important to arrange for the return movement of cam 120 which indexes cassette to be delayed until plunger 60 has been retracted fully from cassette 200.

Figure 11:
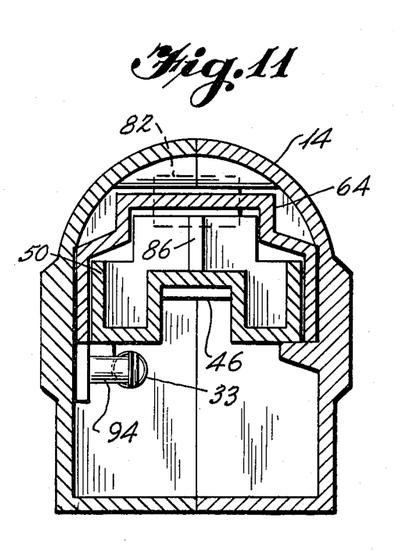
FIG. 11 is an end section taken through line 11—11 on FIG. 1.

The travel by both yoke 22 and cam 120 is generated by movement of the index bar 64, whose structure may best be seen on FIGS. 4, 10 and 11. Index bar 64 overlies and straddles the rack bar 50 to which plunger 60 is attached. Rack bar 50 and index bar 64 move independently. The cam 120 is integrally secured on index bar 64, being a hook-like appendage to a forward end extension 115 on index bar 64 (see FIG. 5).

When trigger 16, is pulled and sector gear 36 causes bull gear 42 to advance rack 46 and with it rack bar 50, only the rack bar 50 advances until the front face 52 on rack bar 50 engages a downwardly extending lip 62 at the front of index bar 64, and thereafter both index bar 64 and plunger 60 advance together (the predetermined distance traveled by cam 120).

Figure 6:
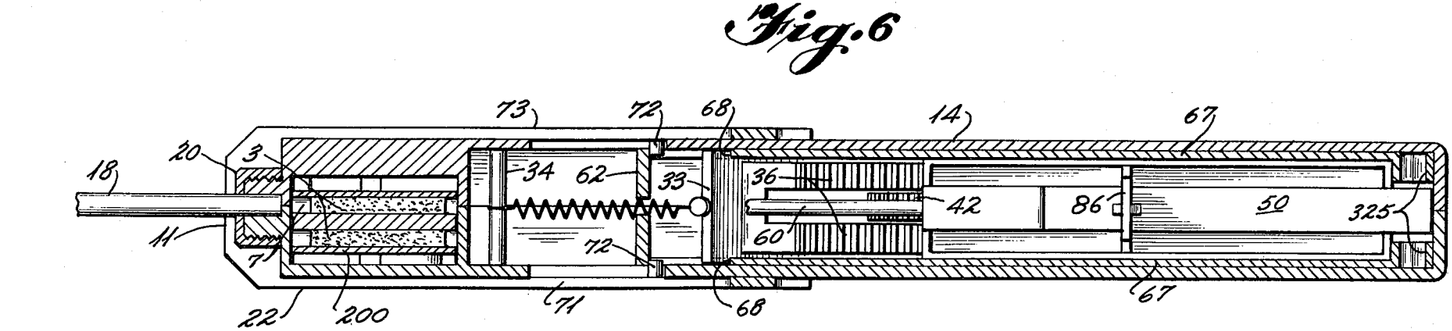
FIG. 6 is a top section taken through line 6—6 of FIG. 2.
Figure 7:
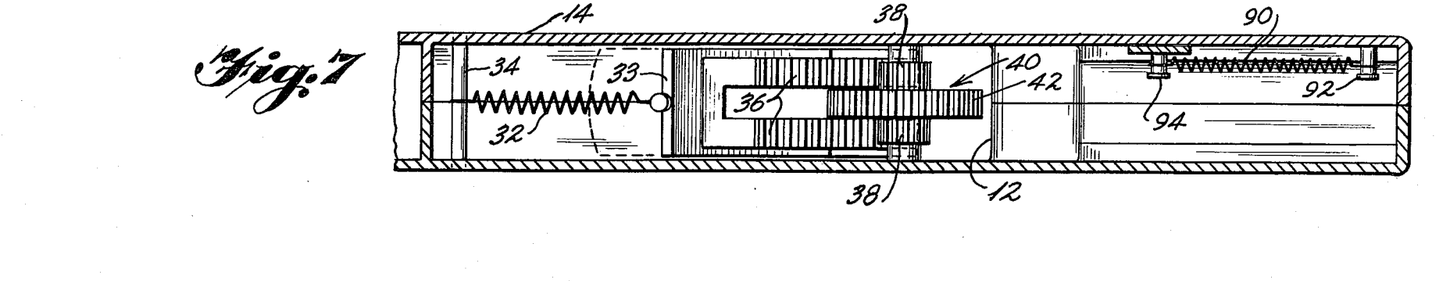
FIG. 7 is a top section taken through line 7—7 of FIG. 2.
Figure 8:
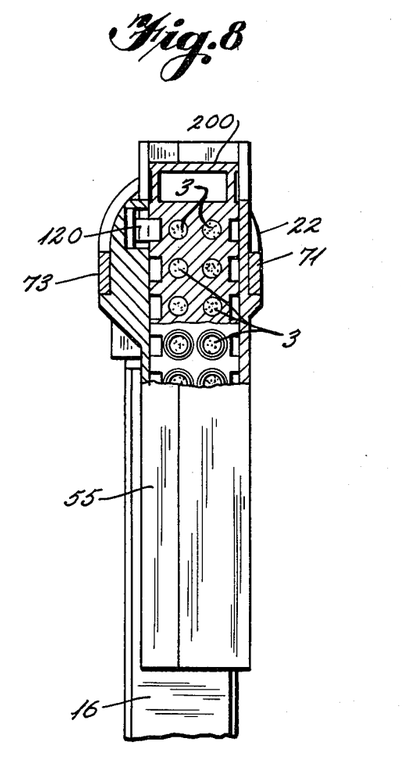
FIG. 8 is an end section taken through line 8—8 on FIG. 1.
Figure 9:
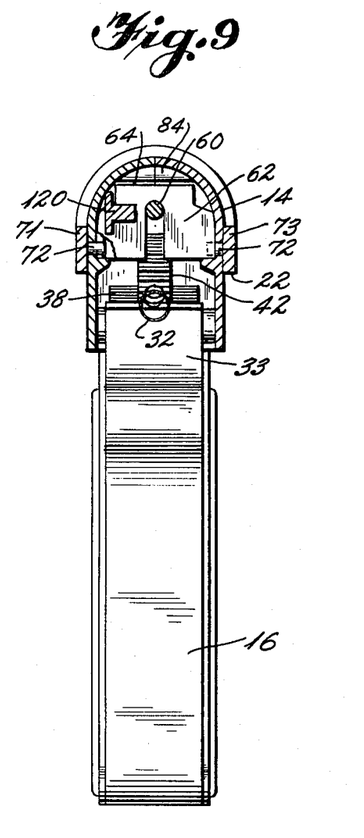
FIG. 9 is an end section taken through line 9—9 on FIG. 1.

It may be seen on FIGS. 4, 6 and 9, that lip 62 is located just ahead of the pair of pins 72 that form part of yoke 22. To repeat, index bar 64 straddles rack bar 50, placing side legs 67 on index bar 64 alongside housing 14 positioned between rack bar 50 and the housing wall (see FIGS. 10 and 11). The side legs 67 of index bar are provided with the aforementioned slots 68 (FIG. 4) slots 68 being just to the rear of front lip 62 in line with a pair of slots 70 in the side walls barrel 14; the pins 72 of yoke 22 seat in slots 70 and 68, as can be seen in FIG. 9.

The yoke 22 (the structure of which is most clearly illustrated in FIGS. 1, 2 and 3), rides then on the outside surface of housing 14. Yoke 22 is formed from a pair of side pieces 71, 73 which carry the front face piece 23 at their forward ends. At the rear of side pieces 71, 73 is a guard 75 that rides on the top of housing 14. The pins 72 that seat in slots 68 and 70 are at the inside surfaces of side pieces 71 and 73 (see FIG. 9). The pins 72 mount yoke 22 to barrel 14.

As has already been pointed out, the length of slots 68 in index bar 64 are set to provide the required degree of lost motion between the movements of index bar 64 and of yoke 22. When index bar 64 has advanced to the point when the ends of slots 68 strike pins 72 on yoke 22, the yoke 22 is moved forward by the further advance of index bar 64, such movement being shown in the sequence of FIGS. 16, 17 and 18. To repeat, yoke 22 begins forward movement just about when the plunger 60 has completely transferred the pellet(s) 3 from their chamber in cassette 200 into needle 18, and then as yoke 22 moves its predetermined travel distance forcing removal of needle 18 from the animal, the plunger 60 which still is traveling forward, forces the pellet(s) out the front end of needle 18 into the needle track 19 being left by withdrawal of needle 18. The size and movement of plunger 60 is such that all of the medicament is deposited beneath the skin of the animal. However, the distance travelled by yoke 22 is, of course, made independent of that travelled by the plunger 60 or by cam 120 by the lost motion connections.

The hereinabove described lost motion connection between index bar 64 and rack bar 50, and between index bar 64 and yoke 22 presupposes that the distance travelled by cam 120 exceeds the distance travelled by yoke 22. If desired, the applicator may be modified to provide for the longer travel by yoke 22, as for example, by changing the lost motion arrangement so that it is a pin and slot connection to the rack bar 50 which moves yoke 22, such a modification being well within the skill of the art, and need not be described here.

In any event, after implantation of the medicament pellets 3 has been completed, and trigger 16 is released tension spring 32 returns the trigger forward and therewith generates reverse movement of sector gear 36, pinion 38 and bull gear 42 which returns rack bar 50 and plunger 60 to their initial at rest position. However, reverse movement of rack bar 50 does not generate a like immediate reverse movement by index bar 64.

Since indexing of cassette 200 which takes place on the reverse movement by cam 120 takes place only after plunger 60 has been retracted from needle 18 and the cassette chamber, the index bar 64 is retained temporarily in its forward position and with it, yoke 22 and cam 120 while almost all of the reverse movement of rack bar 50 and plunger 60 occurs. Index bar 64 is retained by the latching mechanism shown in FIG. 4. When index bar 64 advances to its extreme forward position springable latch 82 passes under a detent 84 which then acts on latch 82 to lock index bar 64 in its forward position. Thus, plunger 60 and rack bar 50 retract until after plunger 60 has cleared the cassette chamber without movement by index bar 64. Just before rack bar 50 completes its retraction movement, a cam rise 86 appropriately positioned on the top of rack bar 50 strikes latch trip 88 to depress latch 82 from detent 84 and free index bar 64 for rearward retraction movement.

A tension spring 90 mounted between pin 92 secured to housing 14 and pin 94 secured to one of the side legs 67 of index bar 64, acts to retract index bar 64 and of course, the cam 120 mounted thereon, which return movement by cam 120 indexes cassette 200 the transverse distance of one chamber has already been described. On retraction of index bar 64, the yoke pins 72 and yoke 22 are also retracted to their rest position.

A buffer spring 325 at the rear of index bar 64 cushions the shock of the spring biased return of index bar 64, and counters the spring force of spring 90 so that the front face 122 of cam 120 can easily slip into and out of its detent position in the cam tracks when cassette 200 is being inserted into housing 55 in applicator 10.

We claim:

1. A pistol-like implanter device for implanting pellets into domestic animals which comprises:

a hollow needle adapted for insertion into a domestic animal mounted at the forward end of said implanter;

a passthrough chamber containing at least one pellet therein positioned to the rear of said needle in line with the bore thereof whereby such a pellet may be expelled from said chamber through the bore of said needle for implantation in a domestic animal;

a trigger means and a plunger means operatively connected whereby when said trigger means is pulled said plunger advances through said chamber into the bore of said needle expelling thereby said pellet, and thereafter retracts when said trigger means is released;

cam means connected to said plunger means to advance when said plunger means advances, to retract only after said plunger means has retracted sufficiently to clear said chamber; and cam track means associated with said chamber wherein said cam rides, said cam and cam track being means to shift said chamber out of line with said needle upon retraction movement to place in line a successor chamber;

a passthrough cam track slot in the side wall of said cassette alongside each chamber;

a diagonal cam track slot connecting adjacent passthrough cam track slots, whereby said cam traverses a passthrough slot during advancing movement, then on retraction movement is directed through the diagonal cam track slot to the next adjacent passthrough cam track slot, serving thereby to shift the cassette chamber by chamber whereby each chamber of the row may be emptied by successive pulls of said trigger.

2. The implanter device of claim 1 further including latching means adapted to lock said cam means against retraction from its advanced position, said latching means being releasable by said plunger after retraction thereof from said chamber.

3. A pistol-like implanter device for implanting pellets into domestic animals which comprises:
  a hollow needle adapted for insertion into a domestic animal mounted at the forward end of said implanter;
  a passthrough chamber containing at least one pellet therein positioned to the rear of said needle in line with the bore thereof whereby such a pellet may be expelled from said chamber through the bore of said needle for implantation in a domestic animal;
  a trigger means and a plunger means operatively connected whereby when said trigger means is pulled said plunger advances through said chamber into the bore of said needle expelling thereby said pellet; and
  needle ejector means mounted at the base of said needle movable relative to said needle operatively connected to said trigger means so as to advance along said needle when said plunger means advances through the bore of said needle, thereby forcing withdrawal of said needle from the domestic animal just as said plunger means expels the pellet from said needle whereby the pellet becomes implanted within the domestic animal in the needle track;
  the said implanter device further comprising cam means operatively connected to said plunger means to advance as said plunger means advances and to retract only after retraction of said plunger means from said chamber said cam means having as it purpose shifting a fresh pellet-containing chamber into line with the bore of said needle during retraction thereof.

4. The implanter device of claim 3 including lost motion means whereby the advance of the plunger means is greater than the advance of said cam means and than the advance of said yoke means.

5. A cassette for implantation pellets comprising a case with two rows of passthrough chambers therein superposed chamber after chamber with equidistant spacing between chambers, each chamber being adapted to contain at least one implant pellet therein;
  said case having thereon a rectalinear side wall alongside each said row of passthrough chambers;
  a passthrough cam track slot in the side wall of said case alongside each chamber of each row;
  a diagonal cam track slot connecting adjacent passthrough cam track slots, whereby a cam forming part of a pellet implantation device may traverse a passthrough cam track slot during movement in one direction, then on reverse movement be directed into the diagonal cam track slot to the next adjacent passthrough cam track slot, serving thereby to shift the cassette chamber by chamber whereby each chamber of a row may be emptied in succession.

6. The cassette of claim 5 wherein the cam track slots on the cassette sides are reversed one from the other, whereby after one row of chambers is emptied of pellets, a 180° shift of the cassette allows for emptying the pellets from the second row of chambers by the aforementioned cam.

* * * * *

UNITED STATES PATENT AND TRADEMARK OFFICE
CERTIFICATE OF CORRECTION

PATENT NO. : 4,447,223
DATED : 5/8/84
INVENTOR(S) : GORDON E. KAYE, EUGENE B. SCHWARTZ, IRVING V. SOLLINS

It is certified that error appears in the above-identified patent and that said Letters Patent are hereby corrected as shown below:

On the Title Page at (73) where the Assignee is indicated, please change "CCT Associates, Bethesda, Md." to --IVY-GENE CO., INC., Washington, D. C.--

On the Title Page at (56) where Attorney, Agent, or Firm is indicated, please change "Cantor and Lessler" to --Fidelman, Wolffe and Waldron--

Signed and Sealed this

Fourteenth Day of August 1984

[SEAL]

Attest:

Attesting Officer

GERALD J. MOSSINGHOFF

Commissioner of Patents and Trademarks